United States Patent [19]
Anderson et al.

[11] Patent Number: 5,376,103
[45] Date of Patent: Dec. 27, 1994

[54] ELECTRODE SYSTEM FOR IMPLANTABLE DEFIBRILLATOR

[75] Inventors: Kenneth M. Anderson, Bloomington; Theodore P. Adams, Edina; Charles G. Supino, Arden Hills; Mark W. Kroll, Minnetonka, all of Minn.

[73] Assignee: Angeion Corporation, Plymouth, Minn.

[21] Appl. No.: 854,862

[22] Filed: Mar. 19, 1992

[51] Int. Cl.$^5$ ............................................. A61N 1/39
[52] U.S. Cl. ................................................... 607/5
[58] Field of Search .............. 128/419 D; 607/5, 123, 607/4

[56] References Cited

U.S. PATENT DOCUMENTS

| | | | |
|---|---|---|---|
| 4,548,203 | 10/1985 | Tacker, Jr. et al. | 128/419 D |
| 4,662,377 | 5/1987 | Heilman et al. | 128/419 D |
| 4,727,877 | 3/1988 | Kallok | 128/419 D |
| 4,817,608 | 4/1989 | Shapland et al. | 128/419 D |
| 4,944,300 | 7/1990 | Sakesena | 128/419 D |
| 4,953,551 | 9/1990 | Mehra et al. | 128/419 D |
| 5,050,601 | 9/1991 | Kupersmith et al. | |
| 5,083,562 | 1/1992 | de Coriolis et al. | 128/419 D |
| 5,107,834 | 4/1992 | Ideker et al. | 128/419 D |
| 5,111,811 | 5/1992 | Smits | 607/5 |
| 5,133,353 | 7/1992 | Hauser | 128/419 D |
| 5,209,229 | 5/1993 | Gilli | 607/122 |
| 5,261,400 | 11/1993 | Bardy | 607/5 |

OTHER PUBLICATIONS

Jones et al., "Internal Cardiac Defibrillation in Man: Pronounced Improvement with Sequential Pulse Delivery to Two Different Lead Orientations", Circulation, vol. 27, No. 3, Mar., 1986, pp. 484-491.

Primary Examiner—Angela D. Sykes
Assistant Examiner—Kennedy J. Schaetzle
Attorney, Agent, or Firm—Patterson & Keough

[57] ABSTRACT

A defibrillator pulse generator for pectoral implant utilizing the metal case as an electrode and operative to supply unique patterns of monophasic, biphasic, or pairs of electrical pulses to the connected electrodes.

12 Claims, 6 Drawing Sheets

| PATTERN NUMBER | ELECTRODES AND POLARITIES | | | |
|---|---|---|---|---|
| | RVA | SVC | CAN | SUB |
| 1 | − | + | + | + |
| 2 | − | + | − | − |
| 3 | + | − | − | − |
| 4 | + | − | + | + |

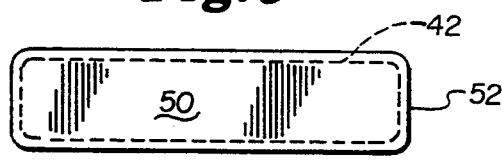
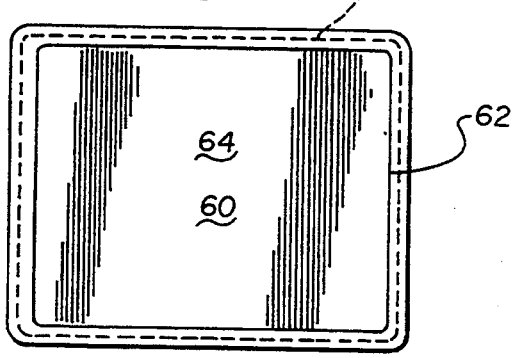
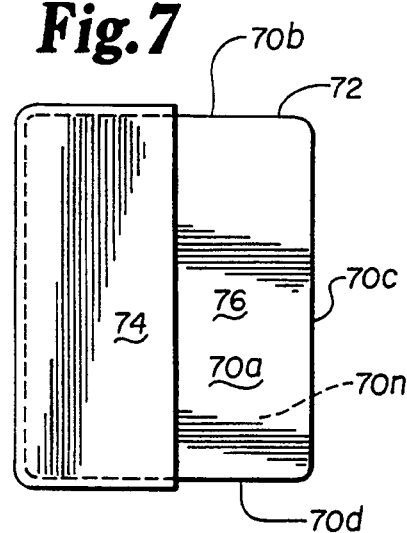
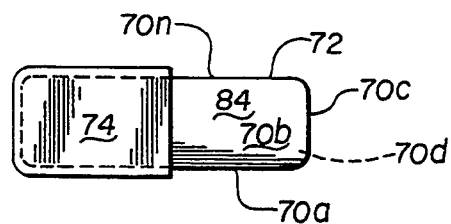
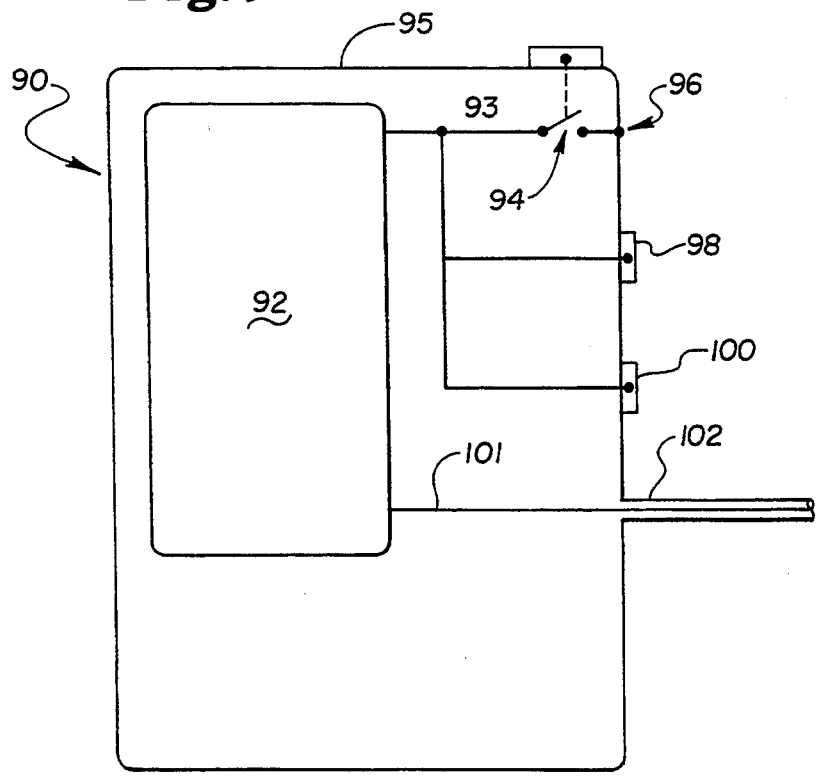

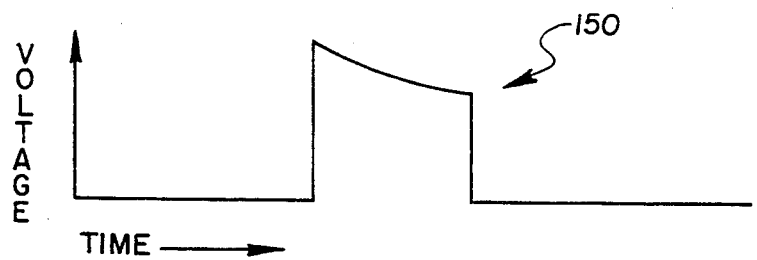
Fig. 11
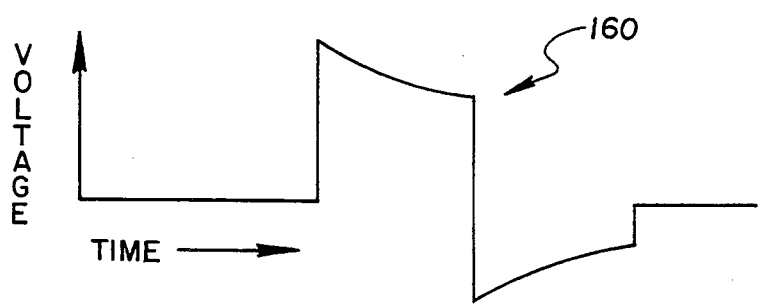
Fig. 12
Fig. 13
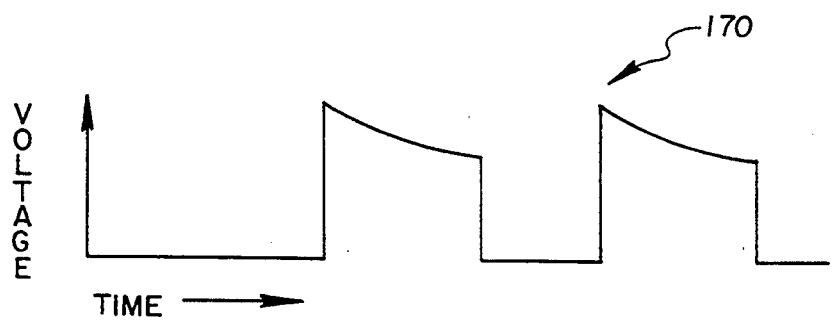

| PATTERN NUMBER | ELECTRODES AND POLARITIES ||| |
|---|---|---|---|
| | RVA | SVC | CAN |
| 1 | − | + | + |
| 2 | − | 0 | + |
| 3 | + | − | − |
| 4 | + | 0 | − |

180

| PATTERN NUMBER | ELECTRODES AND POLARITIES ||| |
|---|---|---|---|
| 5 | 0 | + | − |
| 6 | 0 | − | + |

| PATTERN NUMBER | ELECTRODES AND POLARITIES | | | |
|---|---|---|---|---|
| | RVA | SVC | CAN | SUB |
| 1 | − | + | + | + |
| 2 | − | + | − | − |
| 3 | + | − | − | − |
| 4 | + | − | + | + |

Fig.18

| PATTERN NUMBER | ELECTRODES AND POLARITIES | | | |
|---|---|---|---|---|
| 5 | 0 | − | + | + |
| 6 | 0 | + | − | − |

ELECTRODE SYSTEM FOR IMPLANTABLE DEFIBRILLATOR

BACKGROUND OF THE INVENTION

1. Field of the Invention

This invention relates to implantable defibrillator systems, and particularly to the electrodes and pulse generators used with such systems.

2. Description of the Prior Art

The departure of the heart from normal action to uncoordinated and ineffectual contractions "fibrillation" can lead to death within minutes unless corrected. One method of treatment to restore the normal heart action involves passing electrical current through the heart muscle. The effectiveness of such treatment is dependent on a number of factors, including the location of the electrodes used to apply the electrical current, the shape of the electrodes, and the magnitude, timing, and waveform of the current. While all these factors are significant, a fundamental problem of all such electrical treatments arises from the fact that they all require large currents, several amperes to accomplish defibrillation. And, because the heart muscle typically presents an electrical impedance in the range of 40 to 100 ohms, signal amplitudes of several hundred volts are required to obtain the necessary current. The requirements for relatively high voltage and several-ampere currents combine to place great importance on efficient, low-resistance electrode arrangements for delivering the defibrillation signal to the heart. Ideally the electrode would have no resistance itself and would be placed directly against the heart muscle to avoid the voltage drop across the tissue that surrounds the heart.

Various approaches to the optimal electrode have been attempted. For example, the epicardial-patch electrodes comprise conductive and relatively large-area elements stitched directly onto the exterior of the heart itself. While this approach is satisfactory from the electrical standpoint, the attachment of the electrodes requires a major surgical procedure, such as opening the chest cavity and exposing the heart, as depicted schematically in FIG. 1. Aside from the danger that such surgery presents to all patients, many patients who require this treatment are in such poor condition that this procedure presents an unacceptable risk. In situations where such radical surgery is inappropriate, other, less effective, electrode configurations have been used. For example, the transvenous technique utilizes a conducting filament threaded through an opening in a vein, and into the heart interior. When the filament coils up in a heart chamber, ideally against the chamber wall, a relatively large-area contact to the cardiac muscle can be made. This approach requires that two such electrodes be used, one in the right-atrium (RA) position or in the nearby superior vena cava (SVC) position, and the other placed at the right-ventricular-apex (RVA) position. Despite the fact that transvenous electrodes can be inserted with a relatively simple surgical procedure, they have a serious shortcoming. Because of the design constraints that permit them to be threaded through the blood vessels, they cannot be depended upon to make adequate contact with the interior wall of the heart, and therefore they sometimes do not direct adequate current through a sufficient portion of the heart-muscle volume to achieve defibrillation.

Another option is to combine a transvenous electrode with a subcutaneous patch (SUB) in the fashion described in U.S. Pat. No. 4,817,608 to Shapland, and in U.S. Pat. No. 4,953,551 to Mehra. This approach implants a shallow, just-under-the-skin conductive element of appreciable area on the patient's left side to serve as an electrode, as illustrated in FIG. 2. Since the patch is not directly on the heart, current must pass through the intervening body tissue and fluid to reach the heart. The resistance of the intervening tissue and fluid requires the application of a higher voltage to achieve the desired current through the heart muscle, and the passage of the current through the intervening material may lead to patient discomfort. Additionally, while the surgical procedure for implanting the subcutaneous patch is relatively minor compared to that required for implantation of electrodes directly against the heart muscle, it still presents some risk to the patient. Although the subcutaneous-patch approach provides the advantage of simpler and less risky surgery, the proximity of a subcutaneous patch to the body's surface leaves the electrode relatively unprotected, and as a result, such electrodes have been subject to flexure and breakage from mishaps, and even from normal body motions.

Many patients have experienced ventricular fibrillation, or are likely to experience it. These patients are best treated by a defibrillator that is implanted in the body. Because of the relatively high voltage and substantial currents involved in treatment, the size and weight of the implanted pulse generator (PG) is an important factor. The term PG is used to identify the single package or module that contains the entire implanted defibrillator system, excluding only its electrodes and associated electrical leads. The package is usually a sealed housing made of titanium, selected for its relatively light weight and corrosion resistance. The weight of the PG is normally in excess of 200 grams, or roughly half a pound. While electrical efficiency would be better served with pectoral implantation, the size and weight of the PG usually precludes this location for cosmetic and comfort considerations, and the more spacious abdominal cavity is normally the chosen implantation site. This, of course, is in spite of the fact that PG implantation nearer the heart would result in a more compact system, with shorter leads.

Implantation of the PG nearer the heart provides the advantage of a more efficient system which in turn allows the size of the PG to be reduced. PG implantation near the heart also permits various new electrode arrangements, which are the subject of the present invention. In particular, it permits use of the metallic PG housing as an electrode (hereinafter abbreviated as "CAN". This is, in a sense, a "free" electrode since the housing is required in any case. While use of the PG enclosure as an electrode is suggested in U.S. Pat. No. 4,727,877 to Kallok, the resulting consequences were not addressed.

It is anticipated here that electrode use of the pectorally implanted PG housing will be primarily an augmentation of present systems that employ a catheter for one or more purposes. Implanting the PG involves surgery little more invasive than that required to implant a subcutaneous patch. Furthermore, it eliminates the troublesome requirement for tunneling wires under the skin that accompanies the subcutaneous patch, and the PG is also not subject to crumbling and breakage.

It is possible to use the PG enclosure as an electrode in combination with electrodes of the prior art, such as the RVA, SVC and subcutaneous-patch (SUB) electrodes. This facilitates the use of sequential defibrillation pulses having differing spatial axes, demonstrated in the prior art to reduce the amount of energy needed for defibrillation. Energy consumption is a vital concern since it is directly related to size and therefore also implantability. This is discussed in more detail by D. L. Jones, et al., "Internal Cardiac Defibrillation in Man: Pronounced Improvement with Sequential Pulse Delivery to Two Different Lead Orientations", *Circulation*, Volume 73, pages 484–491, March, 1986, and in their U.S. Pat. No. 4,548,203. See also, Saksena, U.S. Pat. No. 4,944,300, and Kallok, U.S. Pat. No. 4,727,877, as well as Tacker, European Patent Application 0,095,726.

SUMMARY OF THE INVENTION

The invention provides system and electrode designs, configurations, and current-application patterns that are simpler, less troublesome, more reliable, more efficient, and also are less risky to the patient, and less costly than those of the prior art.

One objective of the present invention is to accommodate pectoral implantation of a PG, with the PG housing used as an electrode in combination with prior art electrode arrangements. One such arrangement is shown schematically in FIG. 3. This arrangement is more compact than before, and has substantially shorter leads. Eliminating even a portion of the parasitic resistance in the leads (by shortening them) is significant here because of the high peak currents required for effective defibrillation. A platinum or other polarization-decreasing coating for the titanium case has been found to be advantageous.

It will be appreciated that the use of the PG case as an electrode is not possible for abdominal implantations. Use of the PG CAN electrode in an abdominal implant would cause severe and painful shock to the patient. Aside from this, such an arrangement would cause an intolerable energy waste because of the need to push large currents through the diaphragm and portions of the abdominal organs in order to reach the heart.

Another aspect of the present invention is to use the PG-housing electrode both in lieu of the subcutaneous-patch electrode and as an augmentation to it, providing either two, three, or four electrodes. Either case opens wide, new opportunities for a variety of pulse-sequence and pulse-axis combinations, with the second term referring to the spatial direction of the discharge, fixed by polarity and electrode choices.

In pectoral implantation of a PG, the entire PG exterior may be employed as an electrode. This provides a large electrode area, and hence a small parasitic contact resistance. While the low contact resistance is a desirable goal, the system could pose a serious shock hazard to medical personnel handling it before and during implantation. Also, this arrangement would not allow steering the current in a desired direction.

The application of an insulating layer to portions of the PG's external surface largely eliminates the shock hazard and provides the beneficial result of allowing the current to be steered in a direction most advantageous for defibrillation. The PG housing desirably approximates a somewhat flattened rectangular parallelpiped. This geometry allows most of one major face of the housing to serve as the electrode, with the balance being insulated, as is illustrated in FIGS. 4, 5 and 6. Because the four smallest faces, or edges, as well as one major face, of the PG are insulation-covered, safe handling of the PG is comparatively straightforward and can be accomplished without risk to the surgeon during implantation. A further benefit of this arrangement is that the electrical discharge can be aimed in a chosen direction. For example, aiming the discharge toward the interior of the body causes primary current conduction to avoid the skin, which largely avoids the additional discomfort normally accompanying an electrode not in direct contact with the heart. On the other hand, aiming the discharge away from the interior of the body causes the path length, and hence parasitic resistance, to increase, but causes less skeletal muscle "jerk". By this is meant a reflexive contraction of skeletal muscles in the path of the electrical discharge, and stimulated by it, with uncomfortable, and possibly injurious results.

As a further option, another portion of the PG housing could be covered with an insulating coating, as shown in FIGS. 7 and 8. The ease and safety of handling of this configuration approximates that for the preceding option, but additionally provides a wider range of aiming options due to the increased number of surfaces which are not insulated.

While the conductive PG housing will be most advantageously used in the pectoral implant, it can also be used in conventional abdominal implantation by adding a single-pole, single-throw selector switch to the system, as shown in FIG. 9. When selector switch 94 is open, as in FIG. 9, the metal housing of the PG is isolated from all circuitry, and the PG may be conventionally implanted in the abdominal cavity. But when selector switch 94 is closed, the PG housing is activated as the CAN electrode. By the simple act of plugging in the lead from a SUB electrode, and (or) an RA electrode, the surgeon can realize various electrode-pattern options to accompany the pectorally implanted CAN electrode.

In the event that further protection against shock is desired, this invention provides a circuit, shown in FIG. 10, for sensing that the implantation procedure has not yet been performed and develops a disabling signal to prevent inadvertent generation of the defibrillation signal. This feature totally eliminates the shock hazard to medical personnel. It can be viewed as a safety element that augments the exterior insulation described above.

It is evident that combining the PG-housing or CAN electrode with the well-established defibrillation electrodes SVC and RVA, that are often associated with a cardiac catheter, makes possible a number of polarity patterns for applying defibrillation pulses. Beyond this, is the choice of the monophasic pulse pictured in FIG. 11, the biphasic pulse in FIG. 12, and the sequential pulses in FIG. 13. Let it be said that the two pulses in the biphasic waveform, as well as in the sequential waveform are of comparable amplitude and duration, thus avoiding the infinity of possible waveform variations. Let "comparable" be taken to mean "within a factor of four".

Consider first the monophasic pulse. Taking the three electrodes in the sequence RVA, SVC, and CAN, FIG. 14 identifies four polarity patterns that are useful. The number in the left-hand column identifies the pattern. The plus and minus symbols indicate relative polarities of the respective electrodes during discharge, and the zero symbol means that the circuit to the corresponding electrode is open, or else that the electrode is otherwise omitted from the systems. It will be seen that options assigning a zero to the RVA electrode are omitted, because the RVA electrode plays a dominant role in directing current through the bulk of the left-ventricular muscle. Furthermore, it has been found that assigning the same polarity to the RVA and SVC electrodes, that is, making them electrically common, is an ineffective option. Note that simple polarity reversal has been treated as a separate pattern. That is, pattern 3 is the reverse of 1, and 4 is the reverse of 2. Finally, the case with the CAN electrode open or removed is omitted because it reverts to the prior art.

Next, the four patterns in FIG. 14 may be interpreted as a description of the first pulse in the biphasic waveform of FIG. 12. Thus, FIG. 14 deals fully with both the monophasic and biphasic cases. The case of two pulses in sequence involves additional considerations. First, identify a given sequential-pulse option by using the pattern identification numbers. Thus, "12" would mean that the first pulse is of pattern 1, and the second, pattern 2. It has been found that two same-pattern (and otherwise similar) pulses inca sequence are not beneficial. In the sequential-pulse representation of FIG. 13, different polarity patterns are assumed for the two pulses. Therefore, the sequence options 11, 22, 33 and 44 are dropped from consideration. Next, a sequence involving simple polarity inversion on all electrodes in going from the first pulse to the second is also omitted because this simply constitutes one of the biphasic options. This removes 13, 31, 24 and 42. Next, consider that a pattern eliminating the RVA electrode may be useful as one of the two sequential pulses, even though it is not useful in the monophasic case. There are two such patterns given in FIG. 15, and numbered 5 and 6. Thus, it is possible to list exhaustively all useful pattern combinations in the sequential case, as has been done in FIG. 16.

When a subcutaneous-patch or SUB electrode is present in addition to the RVA, SVC, and CAN electrodes, the list of patterns must be reconsidered. Once again, a pattern with RVA and SVC common is rejected for the same reason as before. Further, a pattern with CAN and SUB having opposite polarities is rejected because the current from one to the other would be remote from the heart and wasted. In addition, a pattern with CAN open is avoided because it constitutes prior art, and a pattern with SUB open is also avoided because such cases have already been treated in FIGS. 14, 15 and 16. Thus, there are four patterns again this time, as given in FIG. 17. Again, there are two additional patterns that are potentially useful in the sequential case, as given in FIG. 18. Because the symmetries in FIGS. 17 and 18 are identical to those in FIGS. 14 and 15, it follows that FIG. 16 gives the useful pattern combinations for the case of four electrodes, as well as for the case of three electrodes.

One significant aspect and feature of the present invention is an implantable pulse generator for defibrillation that is lighter in weight, as well as being smaller in size, than those of the prior art, and hence lends itself to pectoral implantation.

Another significant aspect and feature of the present invention is a compact defibrillation system having leads shorter than those of the prior art.

A further significant aspect and feature of the present invention is using the PG's metal housing as an electrode without creating a hazard to medical personnel during implantation, nor undue discomfort to the patient during the defibrillation process.

A further significant aspect and feature of the present invention is a PG metal housing designed to serve as an electrode, but which is partly covered by an insulating layer that has the combined function of providing protection from discharges for medical personnel who handle the system before and during implantation, and of "steering" the electrical current within the body.

Yet another significant aspect and feature of the present invention is the addition of a selector switch to the PG of the invention that will permit its use in a conventional abdominal implantation with conventional electrodes, as well as in the pectoral-implantation option wherein the housing is an electrode.

An even further significant aspect and feature of the present invention is a safety feature involving a comparator circuit that senses metal-housing-to-circuit-common resistance, and disables the PG unless that resistance is low enough to signify system implantation has been completed, further protecting medical personnel before and during surgical implantation.

Yet a further aspect and feature of the present invention is the use of the PG-metallic-housing (CAN) electrode, in lieu of or in combination with a subcutaneous-patch (SUB) electrode, and in combination with the RVA and SVC electrodes, to provide a wide range of polarity-pattern and discharge-axis choices for monophasic and biphasic waveforms, as well as a larger number of pulse-pair combinations for use of the sequential technique.

Having thus described the embodiments of the present invention, it is a principal object hereof to provide a pulse generator for defibrillation that is small enough in size and weight to be suitable for pectoral implantation.

Another object of the present invention is to create an implantable defibrillation system that is compact and comprises leads much shorter than those of the prior art.

A further object of the present invention is to provide a defibrillation electrode that is efficient, well-positioned, and "free" in the sense that it is the CAN or housing of the pulse generator that must in any case be present.

Yet another object of the present invention is to protect medical personnel from hazardous shocks during implantation by partly covering the housing electrode by an insulating layer.

Yet a further object of the present invention is an ability to steer the defibrillating current within the body by insulating selected portions of the housing electrode.

Another object of the present invention is versatility in pulse-generator design, with a selector switch being able to convert it from a module suitable for pectoral implantation with the housing as an electrode to a module suitable for conventional abdominal implantations.

A related object of the present invention is to provide a wide range of polarity pattern and discharge-axis options for monophasic and biphasic defibrillation waveforms, as well as a larger number of pulse-pair combinations for use of the sequential technique.

A further object of the present invention is a safety provision for medical personnel before and during implantation in the form of a comparator circuit that senses output resistance and disables the pulse generator unless that resistance is low enough to signify that implantation has been completed.

Yet another object of the present invention is to provide several polarity-pattern and discharge-axis options by combining the PG-housing electrode with more conventional electrodes such as the RVA and SVC coils on a standard catheter.

Yet a further object of the present invention is to replace the subcutaneous-patch electrode by a PG-housing electrode that eliminates the need for tunneling wires under the skin and eliminates the hazards of breakage and crumbling that accompany the subcutaneous-patch option.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIGS. 4, 5 and 6 illustrate schematic representations of a defibrillating system of the present invention having a PG housing with one major metallic face exposed to serve as an electrode, and the balance of the PG surface area covered by an insulating layer;

FIGS. 7 and 8 illustrate schematic representations of a defibrillating system of the present invention having a PG housing with approximately half its surface area exposed to serve as an electrode, and the balance of the PG surface area covered by an insulating layer;

FIG. 9 illustrates a schematic representation of a defibrillating system of the present invention incorporating a selector switch that permits the PG to serve either in the PG-housing-as-electrode mode or in other conventional modes;

FIGS. 11 illustrates a monophasic waveform that in the present invention is applied to a novel set of electrodes in novel patterns;

FIG. 12 illustrates a biphasic waveform that in the present invention is applied to a novel set of electrodes in novel patterns;

FIG. 13 illustrates a sequential-pulse waveform that in the present invention is applied to a novel set of electrodes in novel patterns;

FIG. 17 illustrates a chart of useful polarity patterns for four electrodes, RVA, SVC, CAN, and SUB, for the cases of monophasic and first-biphasic-pulse waveforms; and, FIG. 18 illustrates a chart of additional polarity patterns for use in sequential-pulse waveforms in the four-electrode case.

DESCRIPTION OF THE PRIOR ART

Figure 1:
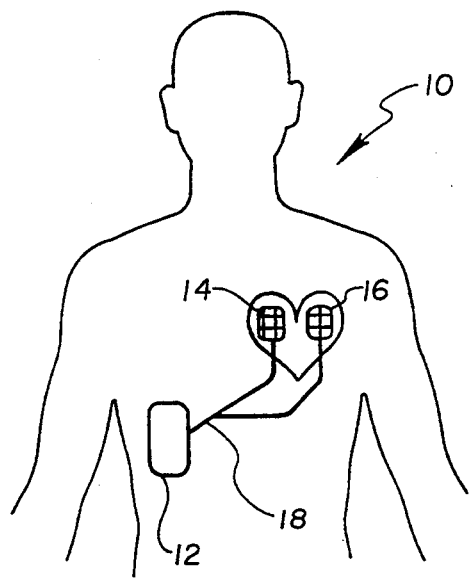
FIG. 1 illustrates a schematic representation of a defibrillating system of the prior art implanted in the abdominal cavity, and having epicardial-patch electrodes attached directly to the heart.

FIG. 1 illustrates a schematic drawing of a patient 10 fitted with a defibrillating system of the prior art consisting of a PG 12 implanted in the abdominal cavity and connected to epicardial-patch electrodes 14 and 16 by electrical-lead harness 18.

Figure 2:
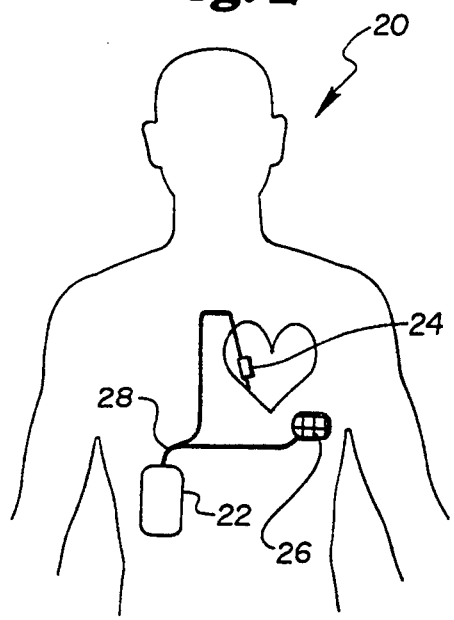
FIG. 2 illustrates a schematic representation of a defibrillating system of the prior art having one transvenous electrode and one subcutaneous-patch electrode.

FIG. 2 illustrates a schematic drawing of a patient 20 fitted with a defibrillating system of the prior art consisting of a PG 22 implanted in the abdominal cavity and connected to transvenous RVA electrode 24 and subcutaneous-patch electrode 26 by means of electrical-lead harness 28 where all numerals correspond to those elements previously described.

DESCRIPTION OF THE PREFERRED EMBODIMENTS

Figure 3:
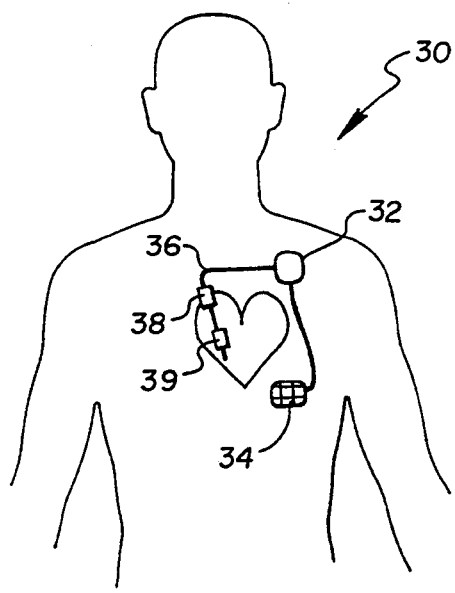
FIG. 3 illustrates a schematic representation of a defibrillating system of the present invention having a SVC electrode, an RVA electrode and one subcutaneous-patch electrode.

FIG. 3 illustrates a schematic drawing of a patient 30 fitted with a defibrillating system of the present invention comprising a pectorally implanted PG 32, a subcutaneous-patch electrode 34, and transvenous catheter 36, carrying an SVC electrode 38, and an RVA electrode 39 where all numerals correspond to those elements previously described.

Figure 4:
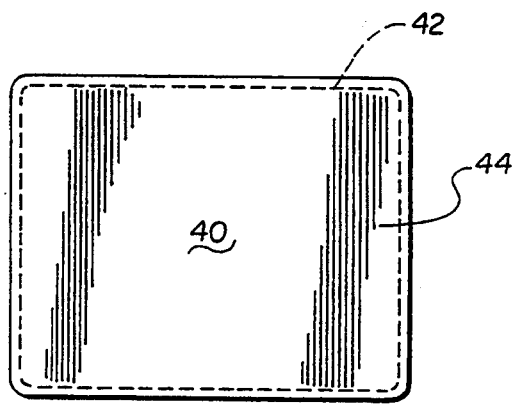

FIG. 4 illustrates the top face 40 of the PG 42 having an insulating layer 44 that covers the entire top surface of the PG exterior where all numerals correspond to those elements previously described.

FIG. 5 illustrates an elevation of a PG 42 having an insulating layer 52 that covers the entire surface of the face 50 depicted, and also covers the remaining three "edge" faces where all numerals correspond to those elements previously described.

FIG. 6 illustrates the bottom face 60 of the PG 42 having an insulating layer 62 that covers only the periphery of the bottom major face 60, leaving the balance 64 of the bottom face 60 within the periphery of the insulating layer 62 to serve as an exposed-metal electrode.

FIG. 7 illustrates a side view of a PG 72, including a plurality of faces 70a–70n, having an insulating layer 74 that covers a significant fraction of the exterior surface of the PG 72, leaving the balance 76 consisting of faces 70a–70n of the exterior surface of the PG 72 in the form of exposed metal to serve as an electrode.

FIG. 8 illustrates a top view of the PG 72 and the insulating layer 74 that covers a significant fraction of the faces 70a–70n, leaving the balance 84 consisting of faces 70a–70n in the form of exposed metal to serve as an electrode.

FIG. 9 illustrates a PG module 90 and represents schematically certain of its internal elements that permit flexible application of the system where all numerals correspond to those elements previously described. The pulse-generator circuit 92 has a first output lead 93 connected through the externally controlled SPST selector switch 94 to the PG housing 95 at the connection point 96. When the switch 94 is open, the PG module 92 can be abdominally implanted in conventional fashion; when the switch 94 is closed, the PG housing 95 can be employed as a defibrillation electrode in the case of pectoral implantation. The first output lead 93 is also connected to a first self-sealing output jack 98 into which an SVC electrode lead can be plugged when desired, as well as to a second self-sealing output jack 100 into which a SUB electrode can be plugged when desired. A second output lead 101 from the pulse-generator circuit 92 is permanently connected inside a lead 102 that is intravenously installed to place an electrode in the RVA position. Activation of an SVC electrode is accomplished by plugging its lead into jack 98, and activation of a SUB electrode is accomplished by plugging its lead into jack 100. With these options, in addition to that provided by selector switch 94, it is evident that the flexibility of the present invention offers the choice of three single-electrode options, of three common-double-electrode options, and one common-triple-electrode option, for a total of seven options for an electrode pattern to deliver a shock directed at the opposing RVA electrode that is connected to the pulse-generator circuit 92 through the lead 102.

Figure 10:
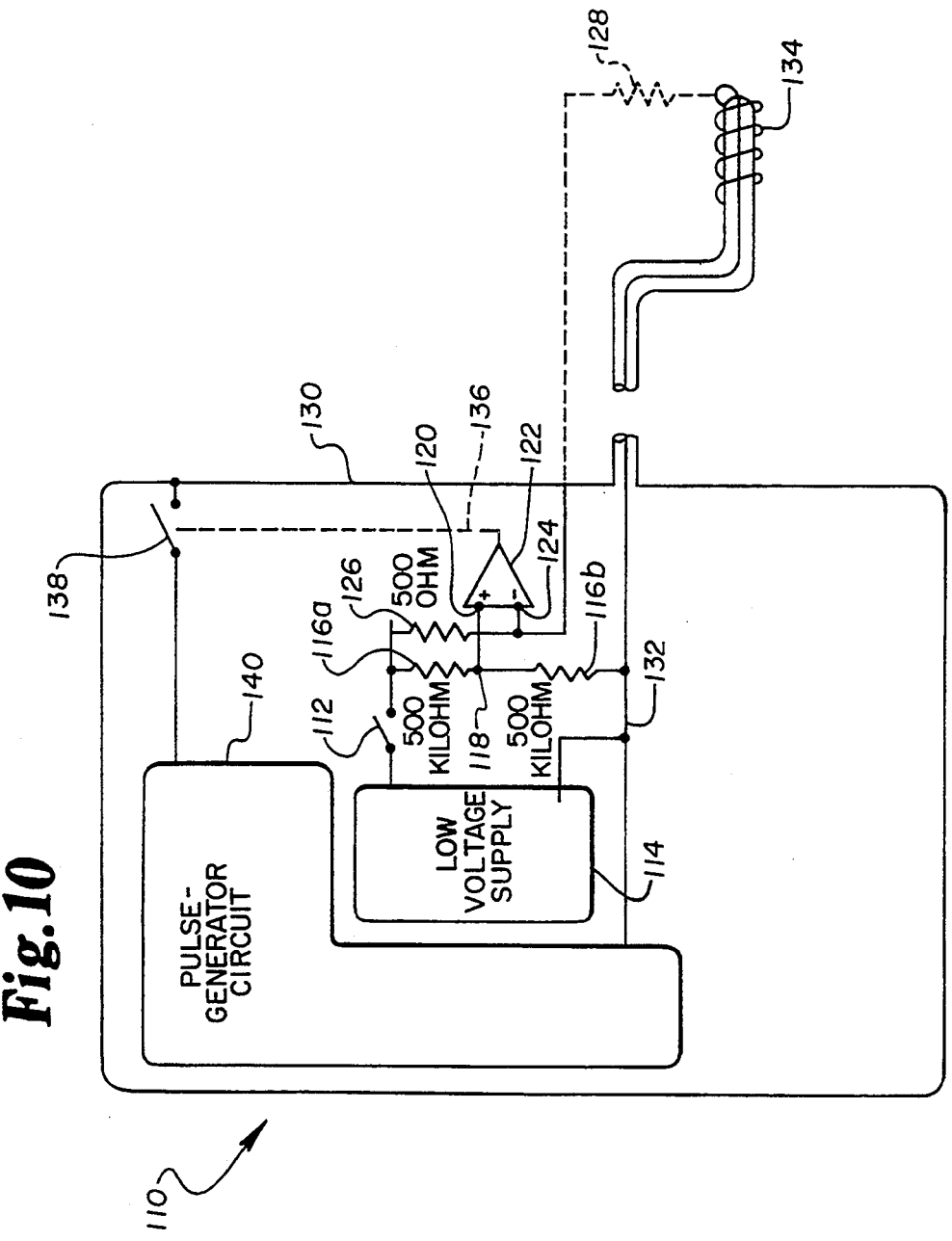
FIG. 10 illustrates a schematic representation of a defibrillating system of the present invention incorporating one possible safety circuit that disables the pulse generator when the housing-to-circuit-common resistance is higher than that encountered by the system after implantation, thus protecting medical personnel who must handle the system before and during implantation.

FIG. 10 illustrates a PG module 110 that incorporates a safety circuit for disabling the pulse generator until the system has been implanted where all numerals correspond to those elements previously described. The safety circuit senses when the system has been implanted by monitoring the resistance between the implanted RVA electrode 134 and the metal housing 130 of the system. When the resistance drops to a low level, the system develops a signal that allows defibrillation pulses to be passed to the CAN or PG-housing electrode.

When the pulse generator 140 is prepared to deliver its pulse or other waveform it closes SPST switch 112 by conventional circuit means. Closing SPST switch 112 causes current from low-voltage power supply 114 to flow through a center-tapped 1-megohm resistor, that is through resistors 116a and 116b. This creates a reference voltage, having a value one half that of the output from the low-voltage supply 114, to be developed across resistor 116a, and causes the centertap 118 to become a reference terminal.

The reference voltage at the centertap 118 is fed to a first, positive, input terminal 120 of comparator 122. A "test" voltage, responsive to the resistance between the CAN electrode metal housing 130 and the RVA electrode 134 is applied to a second, negative, input terminal 124 of comparator 122. This voltage is derived from a voltage divider consisting of a 500-ohm resistor 126 as the "upper" element, and as the "lower" element, the resistance 128 existing at that time from the metal housing of the PG or CAN electrode 130 to the common terminal 132 of the high- and low-voltage circuits, which is also common to the RVA electrode 134. It will be appreciated that, while FIG. 10 illustrates the resistance between the CAN electrode 130 and the RVA electrode 134 as a resistor 128 shown in dotted lines, in actuality, the resistance is not a discrete resistor, but rather the resistance of the path that exists at the time between these electrodes. Before the device is implanted, the path will be largely air and have a very high resistance. However, after implantation, the path will be through relatively highly conductive body tissue, and therefore, have a relatively low resistance.

Even when a person is handling the system, and holding the metal housing of the system in one hand and the RVA electrode in the other, the resistance between circuit points 130 and 134 (from hand to hand) is typically several kilohms, so that the test voltage at negative input terminal 124 is much more positive than the reference voltage at positive input terminal 120, so that the comparator delivers a logical "low" or zero voltage at output terminal 136. This output signal controls the switch 138, and zero voltage to that switch, which is preferably an FET, meaning that the switch is inactivated and hence open. With switch 138 open, the defibrillation pulses from pulse generator 140 are blocked and do not reach the CAN or housing electrode 130.

When the PG module 110 is properly implanted, the electrical path represented by the resistor 128 from the housing electrode 130 to the RVA electrode 134 will lie through body tissue and have a resistance value well below 500 ohms, causing the reference voltage at positive input terminal 120 to be more positive than the test voltage at negative input terminal 124, causing the comparator to switch to the logical "high" condition at output terminal 136. The high signal at comparator output terminal 136 causes switch 138 to close, thereby permitting the normal delivery of the defibrillation pulses from pulse generator 140 to the metal housing 130.

The safety circuit operates for all CAN electrode 130 configurations without modification and functions to prevent accidental shock regardless of the selected pulse polarity. Thus, the medical team is protected in all situations where the shock hazard is present and the safety feature imposes no limitations on the electrode selection, the choice of pulse polarity, or other options such as the pulse sequence or waveform. Further, it is evident that the PG module 110 and its circuitry of FIG. 10 can be combined with the PG module 90 and its circuitry of FIG. 9 by combining the switches 138 and 94 into one switch operable by either of two means.

FIG. 11 illustrates a defibrillation waveform 150 known in the prior art as monophasic that in the present invention is applied to a novel set of electrodes in novel patterns.

FIG. 12 illustrates a defibrillation waveform 160 known in the prior art as biphasic that in the present invention is applied to a novel set of electrodes in novel patterns.

FIG. 13 illustrates a defibrillation waveform 170 comprising a pair of sequential pulses that in the present invention is applied to a novel set of electrodes in novel patterns.

Figures 14, 15, 16:
FIG. 14 illustrates a chart of useful polarity patterns for three electrodes, RVA, SVC, and CAN, describing the cases of monophasic and first-biphasic-pulse waveforms.
FIG. 15 illustrates a chart of additional polarity patterns for use in sequential-pulse waveforms in the three-electrode case.
FIG. 16 illustrates a chart of three- and four-electrode pattern combinations useful in sequential-pulse defibrillation.

FIG. 14 illustrates a chart set 180 of useful polarity patterns for defibrillation using three electrodes: right-ventricular apex (RVA); superior vena cava (SVC); and PG housing (CAN). The set 180 omits patterns that have been found ineffective. The plus and minus symbols indicate relative polarities of the respective electrodes during discharge, and the zero symbol means that the circuit to the corresponding electrode is open, or that the corresponding electrode is otherwise removed from the system. The set 180 is applicable to a monophasic waveform, and to the initial pulse of a biphasic waveform.

FIG. 15 illustrates a chart set 190 of additional polarity patterns for defibrillation using the RVA, SVC and CAN electrode patterns that are for use in one of the pulses in a two-pulse sequential waveform.

FIG. 16 illustrates a chart set 200 of twenty-four pattern combinations for use in sequential-pulse defibrillation. Each digit in the chart refers to the corresponding polarity pattern defined in FIGS. 14 and 15, and each pair of digits represents a sequential-pulse option for two pulses in the case of three electrodes as in FIGS. 14 and 15, and for the case of four electrodes as in FIGS. 17 and 18 which follow.

FIG. 17 illustrates a chart set 210 of useful polarity patterns for defibrillation using the RVA, SVC, CAN, and SUB (subcutaneous-patch) electrodes. The set 210 omits patterns that are known to be ineffective, and is applicable to a monophasic waveform, and to the initial pulse of a biphasic waveform.

FIG. 18 illustrates a chart set 220 of additional polarity patterns for defibrillation using the RVA, SVC, CAN and SUB electrodes, patterns that are for use in one of the pulses in a two-pulse sequential waveform.

Various modifications can be made to the present invention without departing from the apparent scope hereof.

The upper heart electrode can be at other locations, such as locations of the right atrium and coronary sinus.

We claim:

1. A method of operating a defibrillating system comprising:
   a. providing a right-ventricular-apex (RVA) electrode, a superior-vena-cava (SVA) electrode, a pulse-generator case (CAN) electrode, and a subcutaneous patch (SUB) electrode; and,
   b. simultaneously exciting the RVA, SVC, CAN and SUB electrodes according to one of the following pulse-polarity options: $-+++$, $-+--$, $+---$, $+-++$; where plus and minus signs indicate relative polarities of the respective electrodes during discharge.

2. The method according to claim 1 wherein the selected one of the pulse polarity options applies to an initial phase of a biphasic waveform.

3. The method according to claim 1 wherein the pulse-polarity options for excitation of the electrodes additionally include $0-++$ and $0+--$, where the zero symbol means that an electrical circuit to the corresponding electrode is open.

4. The method according to claim 1 wherein the pulse polarity option is for a first pulse of at least two closely spaced sequential pulses and the pulse-polarity options for a second pulse excludes the pulse-polarity option identical to the first pulse and also the pulse-polarity option reversed from the first pulse.

5. A defibrillating pulse generator comprising:
   a. connection for a right-ventricular-apex (RVA) electrode, a superior-vena-cava (SVA) electrode, a pulse-generator case (CAN) electrode, and a subcutaneous patch (SUB) electrode; and,
   b. pulse-generating means for simultaneous excitation of the RVA, SVC, CAN and SUB electrodes according to one of the following pulse polarity options: $-+++$, $-+--$, $+---$, $+-++$; where plus and minus signs indicate relative polarities of the respective electrodes during discharge.

6. The defibrillating pulse generator according to claim 5 wherein the CAN electrode is formed from a metallic housing of the defibrillating pulse generator, and the housing is partially coated with an insulating material.

7. The defibrillating pulse generator according to claim 6 wherein the insulating material extends over an exterior of the housing to leave only one major surface exposed.

8. The defibrillating pulse generator according to claim 6 wherein the insulating material extends over an exterior of the housing to leave more than one surface exposed.

9. The defibrillating pulse generator according to claim 5 wherein the pulse-generating means further comprises means for generating a biphasic waveform and the selected one of the pulse-polarity options applies to an initial phase of the biphasic waveform.

10. The defibrillating pulse generator according to claim 5 wherein the pulse-polarity options for excitation of the electrodes additionally include: $0-++$ and $0+--$.

11. The defibrillating pulse generator according to claim 7 further including selector switch means for disabling the pulse-generating housing as an electrode.

12. The defibrillating pulse generator according to claim 5 wherein the pulse polarity option is for a first pulse of at least two closely spaced sequential pulses and the pulse-polarity options for a second pulse excludes the pulse-polarity option identical to the first pulse and also the pulse-polarity option reversed from the first pulse.

* * * * *